United States Patent [19]
Kim et al.

[11] Patent Number: 5,843,410
[45] Date of Patent: Dec. 1, 1998

[54] POLYMERIC ULTRAVIOLET SCREENING AGENT AND PROCESS FOR THE PREPARATION THEREOF

[75] Inventors: Hyo-Joong Kim; Jong-Tae Lee; Se-Hoon Kang, all of Daejon, Rep. of Korea

[73] Assignee: LG Chemical Ltd., Seoul, Rep. of Korea

[21] Appl. No.: 755,662

[22] Filed: Nov. 25, 1996

[30] Foreign Application Priority Data

Nov. 28, 1995 [KR]  Rep. of Korea ................... 1995 44248

[51] Int. Cl.$^6$ ................ A61K 7/42; A61K 7/00; A61K 31/74
[52] U.S. Cl. .................... 424/59; 424/60; 424/78.02; 424/78.03; 424/400; 424/401
[58] Field of Search ................... 424/59, 60, 400, 424/401

[56] References Cited

U.S. PATENT DOCUMENTS 4,524,061  6/1985  Cho et al. ................... 424/60
4,545,980  10/1985  Hill ........................... 424/60

*Primary Examiner*—Shelley A. Dodson
*Attorney, Agent, or Firm*—Birch, Stewart, Kolasch and Birch, LLP

[57] ABSTRACT

The present invention relates to a novel polymeric ultraviolet(UV) screening agent comprising at least one monomer represented by the following formula (I) in the molecule:

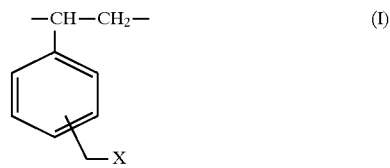

in which X represents the following formula (II) or (III),

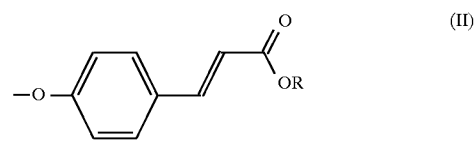

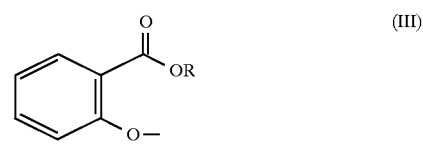

wherein R represents $C_1$–$C_{12}$ alkyl or $C_3$–$C_{12}$ cycloalkyl which can be optionally substituted by $C_1$–$C_6$ alkyl, and to a process for preparing the same.

8 Claims, 3 Drawing Sheets

NMR Data

Macromolecule 8.26ppm(solvent:dichloromethane)

POLYMERIC ULTRAVIOLET SCREENING AGENT AND PROCESS FOR THE PREPARATION THEREOF

BACKGROUND OF INVENTION

1. Field of Invention

The present invention relates to a novel polymeric ultraviolet(UV) screening agent comprising at least one monomer represented by the following formula (I) in the molecule:

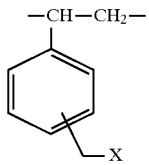

in which X represents the following formula (II) or (III),

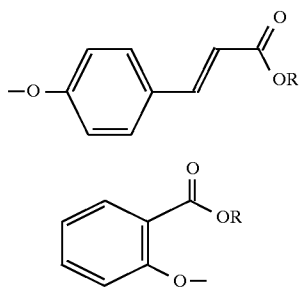

wherein represents $C_1$–$C_{12}$ alkyl or $C_3$–$C_{12}$ cycloalkyl which can be optionally substituted by $C_1$–$C_6$ alkyl.

The present invention also relates to a process for preparing the polymeric UV screening agent as defined above.

2. Background Art

Conventionally, about 1% of sunlight arrived at the surface of the earth is UV light which has a shorter wavelength than visible or infrared light and which is harmful to human body. Since the energy of light is inversely proportional to its wavelength, UV ray has more energy than visible or infrared ray. Therefore, several chemical reactions or physiological changes due to the high energy of UV light can occur as the UV light is irradiated to human body.

The UV light can be classified into three domains according to the wavelength, e.g., UV-A(320~400 nm), UV-B (280~320 nm) and UV-C(200~280 nm). Among them, the UV-C domain has the highest energy and thus gives a harmful influence upon human body. However, it hardly arrives at the surface of the earth because a majority of it is excluded by the ozon layer. The UV-B is a domain which can cause sun burns, that is an immediate damage to human body(skin or hair), due to the solar radiation, and the UV-A is a domain which can give rise to premature aging and erythemata on the skin.

Since the UV light has a high energy, it activates several chemical substances and thus makes them to change their structures or to lose their functions. Specifically, the organic pigment contained in cosmetics, personal care products, etc. is liable to lose their own function by being activated through UV radiation; therefore, a UV screening agent has been necessarily applied to such cosmetics or personal care products during a long period.

On the other hand, as the irradiation amount of UV light against the surface of the earth increases due to the recent disintegration of ozon layer, the market of products to screen UV light has grown rapidly.

Most organic UV screening agents used now have no problem on aspect of their screening function for UV light, but there still remains a problem that they have a property to highly irritate skin. Such a skin-irritation is caused by a permeation of the organic UV screening agents through the skin, thus metallic oxides (for example, titanium oxide and zine oxide), as the inorganic UV screening agents which are widely used now together with an organic UV screening agent, have no irritating property to skin because they cannot permeate skin. However, inorganic UV screening agents have less efficiency for UV screening than the organic ones since they are applied to products from a dispersion technique.

As mentioned above, irrespective of the organic and inorganic UV screening agents, there are undesirable problems when used as they stand. Accordingly, in case of the organic UV screening agents, it has been recently proposed to convert the organic UV screening agents to a macromolecule to inhibit their skin-penetration and a number of relevant prior arts have been reported. Techniques to convert a UV screening agent to a macromolecule can be classified into two categories; one is a polymerization of the UV screening agent itself and the other is a combination of the UV screening agent with side chains of the conventional polymer.

As the methods for preparing a macromolecule by polymerizing the UV screening agent itself, carrying out a radical polymerization reaction by introducing a double bond to the UV screening agent, or polymerizing the UV screening agent by using a highly reactive binder such as polyalkylene oxide, di-acid chloride, etc., are disclosed in U.S. Pat. No. 4,839,160, French Patent No. 2,617,399, U.S. Pat. No. 4,524,061, WO 92-20727, Japanese Patent Laid Open Publication No. 85-99186 and EP Laid Open Publication No. 583,888. However, in case the polymeric UV screening agent is prepared by using the techniques as mentioned above, macromolecules having uniform physico-chemical properties can hardly be prepared because a side reaction which destroys a chromophore moiety of the UV screening agent can occur in the polymerization procedure; and other side reactions may occur in the process for preparing copolymers by using various kinds of monomers.

Since the conventional methods for preparing a macromolecule by polymerizing UV screening agents have a number of disadvantages as discussed above, processes for preparing various macromolecular compounds having thousands to tens of thousands molecular weight by combining chromophores of UV screening agent with the side chains of a polymer, for example organosiloxane, have been developed, and the techniques relevant thereto have been reported in U.S. Pat. No. 4,545,980, EP Lain Open Publication No. 392,882, Japanese Patent Publication No. 88-16416, Japanese Patent Publication No. 89-50711, etc. But, those methods also have a problem that reaction yield of the macromolecule is low.

Thus, on the basis of the above mentioned findings, the present inventors have extensively studied about the combination of UV screening agents with a wide range of polymers in order to develop a polymeric UV screening agent which has an excellent physico-chemical properties and also can be prepared in a high yield. As a result, the present inventors have suprisingly discovered that said problems can be solved by combining a homopolymer of vinylbenzyl chloride(hereinafter referred to as "VBC") or a copolymer of VBC and other monomers with a specific UV screening agent in a chemical process, and thus completed the present invention.

That is, according as a specific UV screening agent and a polymer containing VBC are used for preparing a polymeric UV screening agent in the present invention, the polymeric UV screening agent of the present invention have a number of advantages that it can be prepared in a high yield and in a high purity because there occur no side reactions; it can be well dissolved in oils which are widely used in the preparation of a variety of cosmetics; and it also has a high light absorption efficiency per unit weight. Furthermore, the polymeric UV screening agent can be widely applied to as a UV screening agent having a water resistance since it is such a stable macromolecule that cannot permeate skin and have little hydrophilicity.

Therefore, it is an object of the present invention to provide a novel polymeric UV screening agent comprising at least one monomer represented by the above formula (I) in the molecule.

It is another object of the present invention to provide a process for preparing the novel polymeric UV screening agent as defined above.

BRIEF DESCRIPTION OF THE DRAWINGS

For a thorough understanding of the nature and objects of the invention, reference should be made to the following detailed description taken in connection with the accompanying drawings in which.

DISCLOSURE OF INVENTION

Figure 1:
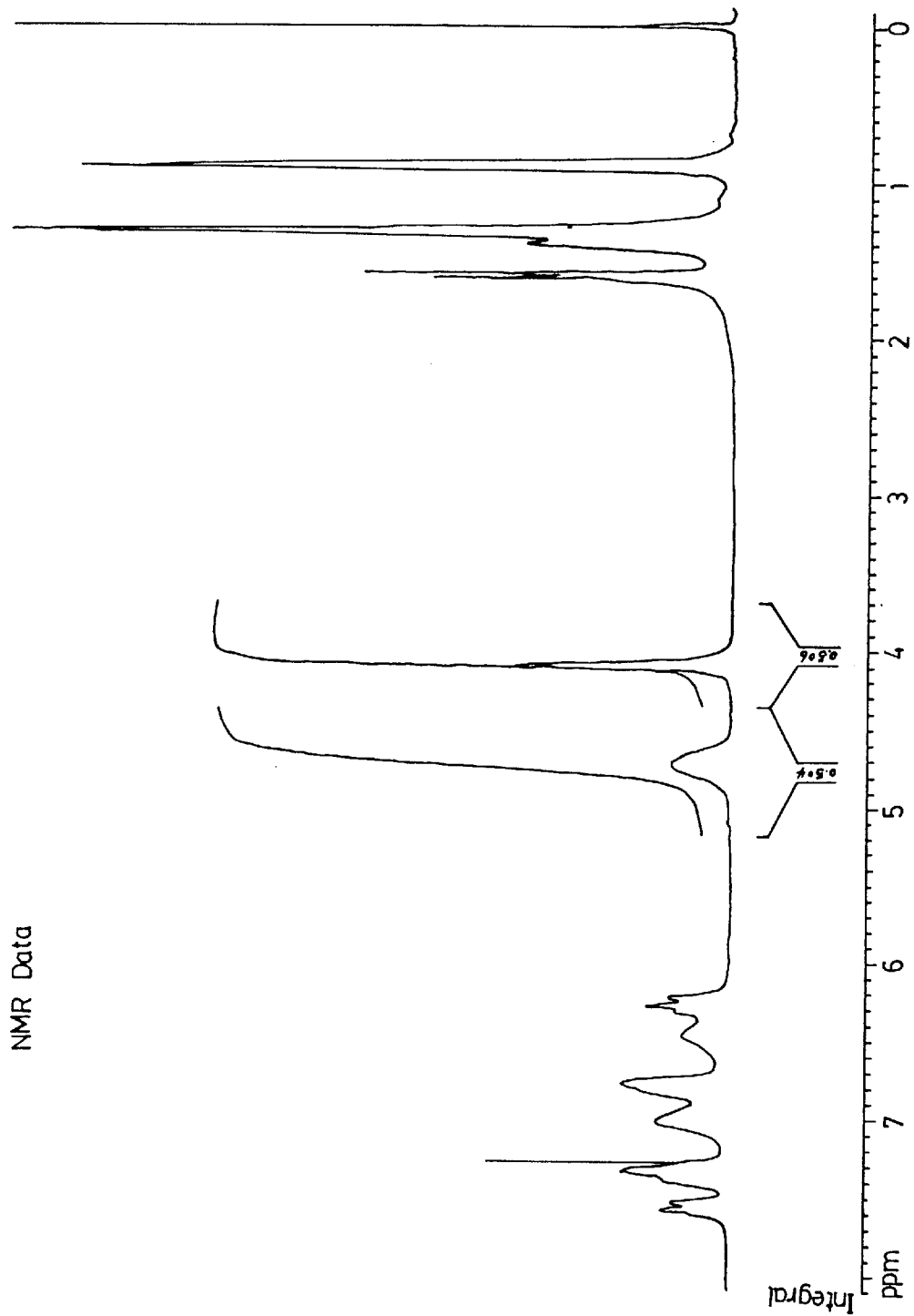
FIG. 1 represents the NMR spectrum of the macromolecule prepared in Example 1 of the present invention.

The term "molecular weight" used herein means a weight average molecular weight.

In one aspect, the present invention relates to a novel polymeric UV screening agent comprising at least one monomer represented by the following formula (I) in the molecule

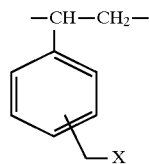   (I)

in which X represents the following formula (II) or (III),

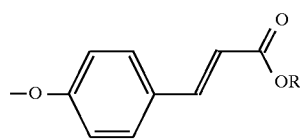   (II)

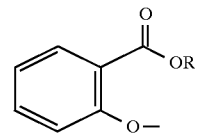   (III)

wherein R represents $C_1$–$C_{12}$ alkyl or $C_3$–$C_{12}$ cycloalkyl which can be optionally substituted by $C_1$–$C_6$ alkyl.

The polymeric UV screening agent according to the present invention is prepared by combining a UV screening agent such as para-oxy cinnamic acid ester derivative or salicylic acid ester derivative, with a polymer comprising at least one VBC unit represented by the following formula (IV) in the molecule

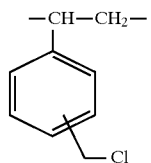   (IV)

The polymeric UV screening agent according to the present invention is a macromolecule having a molecular weight in the range of 1,000 to 1,000,000, preferably 5,000 to 200,000 and also having 5 to 100% by weight of the content of monomer unit (I) therein. In case the molecular weight is less than 1,000 it is no more a macromolecule which cannot penetrate skin, and in case the molecular weight is more than 1,000,000 it becomes a material having no utility since it cannot be easily applied. When the content of monomer unit (I) is less than 5% by weight, the efficacy of the macromolecule as a UV screening agent is diminished because the content of UV absorbing substance to be combined to the polymer is too low. As other monomers which can form a copolymer with VBC in the present invention, one or more selected from vinyl benzene (styrene), ethyl acrylate, 2-ethyl hexyl acrylate, stearyl metacrylate and acrylic acid can be mentioned. A person having ordinary skill in the art to which the present invention pertains can select a preferable monomer to obtain a copolymer having a desired physico-chemical properties and can also determine a preferable copolymerization ratio according to the purposes of usage.

In the second aspect, the present invention also relates to a process for preparing the novel polymeric UV screening agent as defined above.

As depicted in the following reaction scheme 1, the polymeric UV screening agent of the present invention can be prepared by reacting one equivalent of a polymer comprising at least one unit of vinyl benzyl chloride with 1 to 5 equivalents of a UV screening agent in a solvent in the presence of a phase transfer catalyst and a base.

Reaction Scheme 1

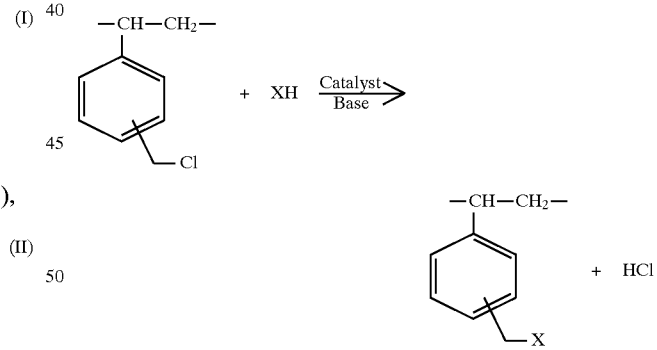

In the above scheme, X is defined as previously described.

According to the above reaction scheme 1, an ether bond is newly formed after a chloride group of the polymer and a hydroxy group of the UV screening agent are reacted. In this case, one or more selected from the organic solvents in which nucleophilic substitution reaction can occur, for example, acetone, dimethylformamide, dimethylsulfoxide, tetrahydrofuran, dichloromethane, chloroform, benzene, etc. can be used as the reaction solvent.

As the catalyst suitable for the above reaction, a phase transfer catalyst, preferably tetrabutyl ammonium iodide, tetrabutyl ammonium bromide, tetrabutyl ammonium hydrogen sulfite or crown ether can be used in an amount of 0.001 to 10% by weight on the basis of the reaction solvent.

When the catalyst is used less than 0.001% by weight it can hardly act as a catalyst because its concentration is too low, and when the catalyst is used more than 10% by weight there is no technical merit because the effect does not increase as the amount of the catalyst increases. In addition, as the base, one or more selected from the metallic carbonates such as potassium carbonate, sodium carbonate, lithium carbonate and the like, the metallic hydrides such as sodium hydride, potassium hydride and the like, and the organic bases such as triethylamine, potassium t-butoxide and the like can be used.

The above reaction can be carried out in a range of normal temperature to the boiling point of the solvent used. In case the reaction is carried out less than 30 minutes, sufficient combining reaction does not occur and a low yield is caused thereby, and in case the reaction is carried out more than 48 hours, it is uneconomic. Therefore, it is preferable to carry out the present reaction for 30 minutes to 48 hours.

The present invention will be more specifically explained in the following examples. However, it should be understood that the following examples are intended to illustrate the present invention ant not to limit the scope of the present invention in any manner.

EXAMPLE 1

To 100 ml of acetone were added 5 g of PVBC (average molecular weight is 55,000), 10 g (34 mmol) of 2-ethylhexyl 4-hydroxy cinnamate, 5 g of potassium carbonate ($K_2CO_3$) and 0.3 g of tetrabutyl ammonium iodide, and then the mixture was reacted for 10 hours while refluxing. 100ml of water was added to the reaction solution, acetone was distilled off therefrom and then the solution was extracted twice with 100 ml of dichloromethane. The extract was subjected to silica gel column chromatography (eluent: dichloromethane) to eliminate the unreacted 2-ethylhexyl 4-hydroxycinnamate and 8.2 g of the polymeric UV screening agent according to the present invention was obtained.

Then, the macromolecule thus prepared was identified by NMR spectrometer, UV spectrometer (Varian), IR spectrometer (Perkin-Elmer) and TLC (Merck) to have the following structure

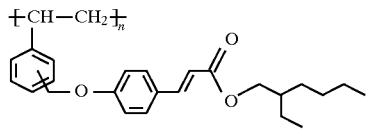

$^1$H NMR (CDCl$_3$, ppm): 0.8–1.0(6 H), 1.2–1.5(10 H), 1.5–1.7(2 H), 4.0–4.2(2 H), 4.6–4.9(2 H), 6.3–7.5(8 H), 6.2–6.3(1 H), 7.5–7.7(1 H)

The protons attached to trans double bond of the cinnamic acid ester are observed at 7.5–7.7 ppm, 6.2–6.3 ppm, and a peak due to the aromatic protons is appeared at 6.3–7.5 ppm. In addition, the benzyl protons newly produced while the hydroxy group of the UV screening agent was introduced in place of the chloride of the polymer are observed at 4.6–4.9 ppm, the methylene protons attached to the oxygen of cinnamic acid ester are observed at 4.0–4.2 ppm, and the remaining alkyl protons are observed between 0.8 and 1.7 ppm. Further, it can be seen that 100% of the substitution reaction has been accomplished on the basis that the peak caused by the benzyl protons of the unreacted chloride are completely disappeared from the above NMR spectrum.

Figure 2:
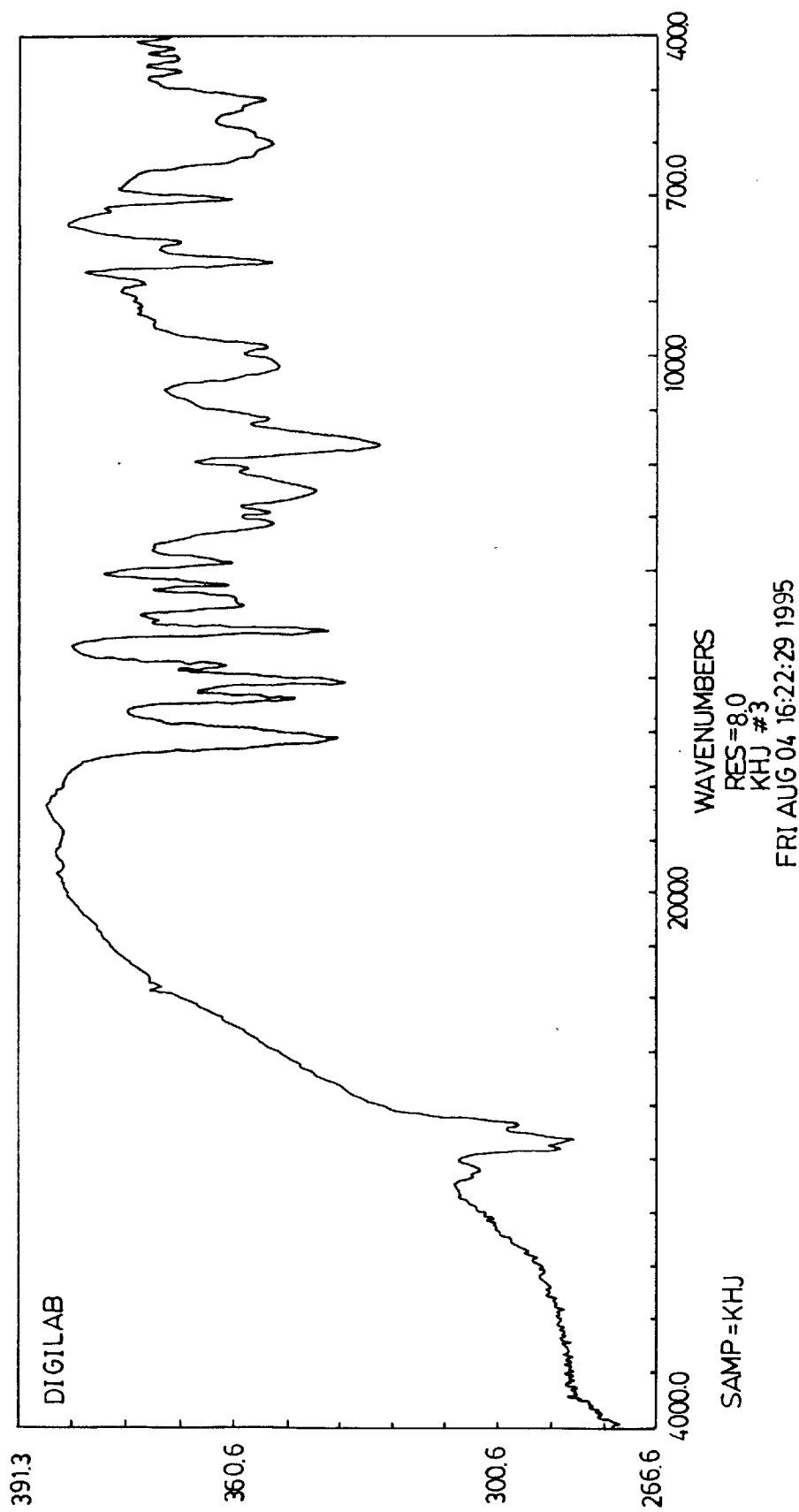
FIG. 2 represents the IR spectrum of the macromolecule prepared in Example 1 of the present invention.

IR (KBr, cm$^{-1}$): 2850, 1700, 1600, 1500, 1250, 1160, 1030 (see, FIG. 2)

A strong absorption peak at 3500 cm$^{-1}$ by the hydroxy group attached to 2-ethylhexyl 4-hydroxycinnamate used as a starting material is disappeared, and an absorption peak by the 2-ethylhexyl group is observed at 2850 cm$^{-1}$. Also, an absorption peak by the ester group and that by the ether bond newly produced are observed at 1700 cm$^{-1}$ and 1250 cm$^{-1}$, respectively.

Figure 3:
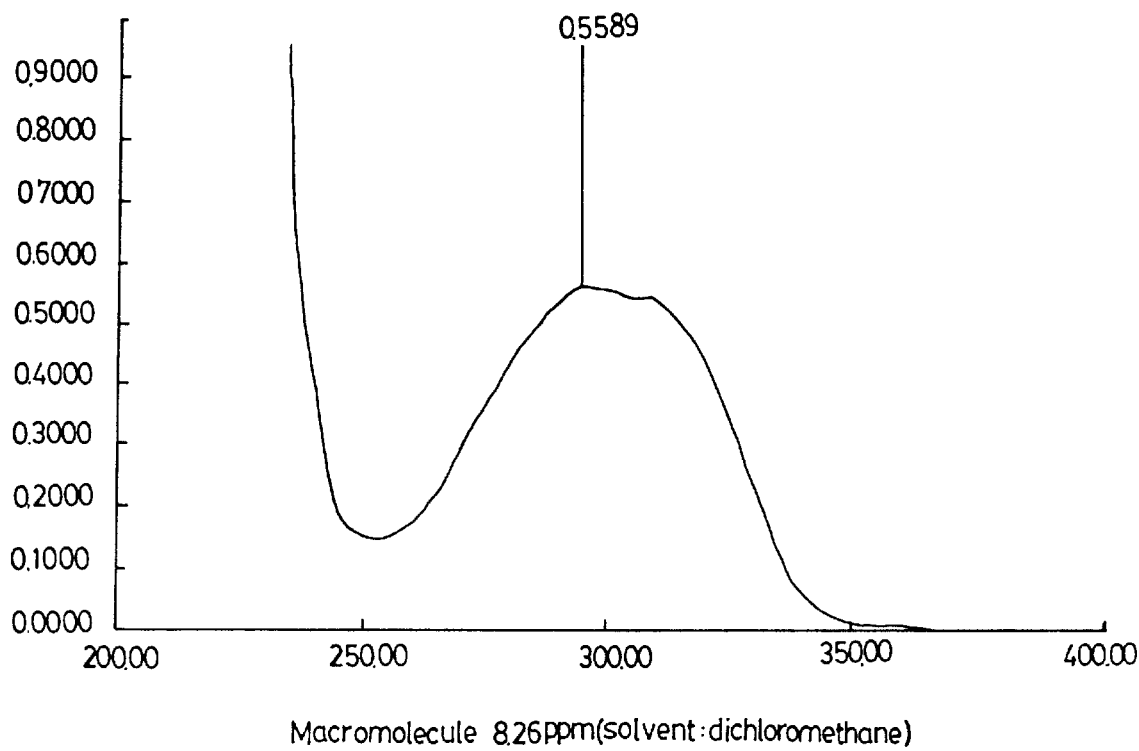
FIG. 3 represents the UV spectrum of the macromolecule prepared in Example 1 of the present invention.

UV: $\lambda_{max}$(nm)=300, absorbance (at a concentration of 10 ppm)=0.67 (see FIG. 3)

The maximum absorption wavelength of the macromolecule was identified as 300 nm which is also the maximum absorption wavelength of para-hydroxy cinnamic acid ester. Therefore, it can be seen that 2-ethylhexyl 4-hydroxycinnamate has been combined to the polymer.

TLC: When dichloromethane is used as a developing solvent, the $R_f$ of PVBC is 1.0, that of 2-ethylhexyl 4-hydroxycinnamate is 0.2, and that of the macromolecule thus prepared is 0.

EXAMPLE 2

To 100 ml of acetone were added 5 g of PVBC (average molecular weight is 15,000), 6.5 g (34 mmol) of ethyl 4-hydroxy cinnamate, 5 g of potassium carbonate ($K_2CO_3$) and 0.2 g of tetrabutyl ammonium bromide, and then the mixture was reacted for 10 hours while refluxing. 100 ml of water was added to the reaction solution, acetone was distilled off therefrom and then the solution was extracted twice with 100 ml of dichloromethane. After the dichloromethane layer was washed with equal volume of water, solvent was eliminated therefrom by distillation under reduced pressure. The residue was crystallized from acetone-water to obtain 6.7 g of the polymeric UV screening agent according to the present invention.

Then, the macromolecule thus prepared was identified to have the following structure by NMR spectrometer, UV spectrometer, IR spectrometer and TLC as Example 1:

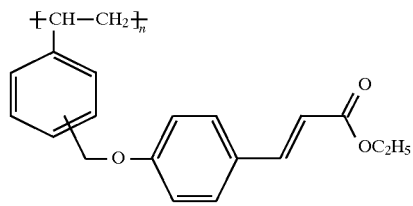

$^1$H NMR (CDCl$_3$, ppm): 7.7–7.5(1 H, broad peak, Ar—CH=CH—CO—), 6.35–6.2(1 H, broad peak, Ar—CH=CH—CO—), 6.35–7.5(8 H, broad peak, Aromatic), 4.9–4.6(2 H, broad peak, Ar—CH$_2$O—Ar—), 4.5–4.2(2 H, broad peak, COOCH$_2$CH$_3$), 1.6–1.2(6 H, broad peak, CH$_2$CH$_3$, —CH (—Ar—)—CH$_2$—)

IR (KBr, cm$^{-1}$): 2850, 1700, 1600, 1500, 1250, 1160, 1030

U: $\lambda_{max}$(nm)=310, absorbance (at a concentration of 10 ppm) =0.65

TLC: When dichloromethane is used as a developing solvent, the $R_f$ of PVBC is 1.0, that of ethyl 4-hydroxycinnamate is 0.2, and that of the macromolecule thus prepared is 0.

EXAMPLE 3

To 100 ml of acetone were added 5 g of PVBC (average molecular weight is 15,000), 6.5 g (26 mmol) of 2-ethylhexyl salicylate, 5 g of potassium carbonate and 0.2 g of tetrabutyl ammonium bromide, and then the mixture was reacted for 10 hours while refluxing. 100 ml of water was added to the reaction solution, acetone was distilled off therefrom and then the solution was extracted twice with 100 ml of dichloromethane. After the dichloromethane layer was washed with equal volume of water, solvent was eliminated therefrom by distillation under reduced pressure. The residue was crystallized from acetone-water to obtain 8.5 g of the polymeric UV screening agent according to the present invention.

Then, the macromolecule thus prepared was identified to have the following structure by UV spectrometer, IR spectrometer and TLC as Example 1:

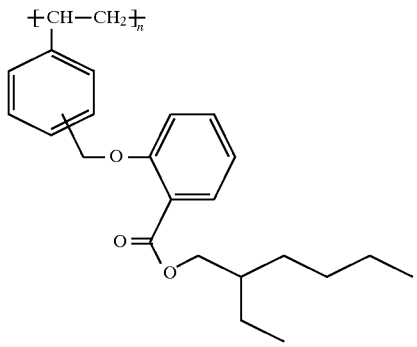

IR (KBr, cm$^{-1}$): 2850, 1700, 1600, 1500, 1250, 1160, 1030
UV: $\lambda_{max}$(nm) =310, absorbance (at a concentration of 10 ppm) =0.65
TLC: When dichloromethane is used as a developing solvent, the $R_f$ of PVBC is 1.0, that of 2-ethylhexyl salicylate is 0.3, and that of the macromolecule thus prepared is 0.

EXAMPLE 4

To 100 ml of acetone were added 7 g of the copolymer of vinylbenzyl chloride(VBC) and vinylbenzene(VB) (VBC:VB =3:1, average molecular weight is 15,000), 10 g (34 mmol) of 2-ethylhexyl 4-hydroxycinnamate, 5 g of potassium carbonate and 0.1 g of tetrabutyl ammonium iodide, and then the mixture was reacted for 10 hours while refluxing. 100 ml of water was added to the reaction solution, acetone was distilled off therefrom and then the solution was extracted twice with 100 ml of dichloromethane. After the dichloromethane layer was washed with equal volume of water, solvent was eliminated therefrom by distillation under reduced pressure. The residue was subjected to silica gel column chromatography (eluent: dichloromethane) to eliminate the unreacted 2-ethylhexyl 4-hydroxycinnamate and 10.5 g of the polymeric UV screening agent according to the present invention was obtained.

Then, the macromolecule thus prepared was identified to have the following structure by UV spectrometer, IR spectrometer and TLC as Example 1:

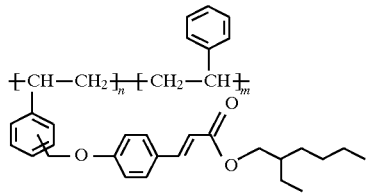

IR (KBr, cm$^{-1}$): 2950, 1700, 1600, 1500, 1250, 1160, 1030
UV: $\lambda_{max}$(nm)=310, absorbance (at a concentration of 10 ppm)=0.41
TLC: When dichloromethane is used as a developing solvent, the $R_f$ of PVBC is 1.0, that of 2-ethylhexyl 4-hydroxycinnamate is 0.2, and that of the macromolecule thus prepared is 0.

COMPARATIVE EXAMPLE 1

Solubility of the novel polymeric UV screening agent of the present invention obtained in Example 1 was determined with respect to several oils widely used in a variety of cosmetics, and the results were compared with that of octyl triazone (CTFA name; commercial name is UVINUL T 150, manufactured by BASF) which is universally used nowadays as a UV screening agent. First, a sample to be tested was dissolved in each oils in several concentrations at an interval of 1% with the help of heating or ultrasonication, then the solution thus prepared was observed with the naked eye after it was allowed to stand for one week at normal temperature for estimating the solubility. Specifically, the solubility was determined on the basis of a transparent solution with no turbidity and phase separation, and the comparision results are described in the following table 1.

TABLE 1

| Oil | Example 1 | Octyl Tiazone |
| --- | --- | --- |
| PEG-7 Glycerylcocoate | >15% | 10% |
| Triethyl citrate | >15% | 8% |
| Caprylic/Capric triglyceride | >15% | 4% |
| PPG-3 Myristyl ether | >15% | 13% |
| Diisopropyl adipate | >15% | 9% |
| Isopropyl myristate | 10% | 3% |
| $C_{12}$-$C_{15}$ Alkyl benzoate | 4% | 4% |

As can be seen from the results of Table 1, since the solubility of the novel polymeric UV screening agent according to the present invention in various cosmetic oils is higher than that of octyl triazone which is the existing typical UV screening agent, the polymeric UV screening agent of the present invention can be more conveniently used specifically when applied to a product in a solution state.

COMPARATIVE EXAMPLE 2

Degree of skin permeation of the polymeric UV screening agent obtained in Example 1 was determined by film-stripping method as explained below, and the result was compared with that of octyl dimethyl PABA (4-dimethylamino-2-ethylhexyl benzoate) which is a UV screening agent universally used nowadays.

That is, the polymeric UV screening agent in Example 1 and octyl dimethyl PABA were dissolved in a solvent mixture of ethanol and n-hexane (75:25, v/v) in a concentration of 0.5%, respectively. Then, 20 $\mu$l of this solution was applied to eight persons' arms, respectively, in the area of 1 to 2 cm diameters. After 30 minutes, horny layer of the skin applied with the above solution was eliminated by using a film (20 X). The film was extracted with 10 ml of 2-propanol, the extract was concentrated to 1 ml and then 50 $\mu$l of this solution was added dropwise to a TLC plate. The TLC plate was developed in dichloromethane and then the amount of the UV screening agent was quantified on the basis of the degree of UV absorption.

As a result of the above test, about 75% of octyl dimethyl PABA was found in horny layer and 25% thereof permeated through the horny layer. In contrast, about 95% of the polymeric UV screening agent according to Example 1 was found in horny layer and it appeared that less than 5% thereof was lost during the extraction procedure.

Therefore, the polymeric UV screening agent of the present invention hardly permeates through the skin when compared with the existing UV screening agent, and thereby it completely overcomes the problem of skin-irritation due to the permeation. Furthermore, since the polymeric UV screening agent is highly soluble to several oils widely used in the preparation of a variety of cosmetics, it can be seen that it is conveniently applied to products.

What is claimed is:

1. A polymeric UV screening agent comprising at least one monomer represented by the following formula (I) in the molecule

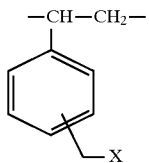
(I)

in which X represents the following formula (II) or (III),

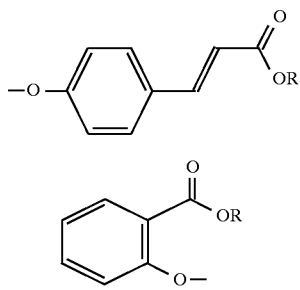
(II)

(III)

wherein R represents $C_1$–$C_{12}$ alkyl or $C_3$–$C_{12}$ cycloalkyl which can be optionally substituted by $C_1$–$C_6$ alkyl.

2. The polymeric UV screening agent of claim 1, wherein the screening agent is a macromolecule having a weight average molecular weight of 1,000 to 1,000,000.

3. The polymeric UV screening agent of claim 1, wherein R is 2-ethylhexyl.

4. A process for preparing the polymeric UV screening agent according to claim 1, wherein one equivalent of a polymer comprising at least one unit of vinyl benzyl chloride is reacted with 1 to 5 equivalents of a UV screening agent in a solvent in the presence of a phase transfer catalyst and a base.

5. The process of claim 4, wherein the solvent is one or more selected from acetone, dimethylformamide, dimethylsulfoxide, tetrahydrofuran, dichloro-methane, chloroform and benzene.

6. The process of claim 4, wherein the phase transfer catalyst is one or more selected from tetrabutyl ammonium iodide, tetrabutyl ammonium bromide, tetrabutyl ammonium hydrogen sulfite and crown ether.

7. The process of claim 4 or 6, wherein the catalyst is used in an amount of 0.001 to 10% by weight on the basis of the solvent.

8. The process of claim 4, wherein the base is one or more selected from potassium carbonate, sodium carbonate, lithium carbonate, sodium hydride, potassium hydride, triethylamine and potassium t-butoxide.

* * * * *